United States Patent [19]

Baumgartner

[11] Patent Number: 4,700,692

[45] Date of Patent: Oct. 20, 1987

[54] SURGICAL IMPLANTATION METHOD AND APPARATUS

[76] Inventor: George C. Baumgartner, 41450 North West Lake Ave., Antioch, Ill. 60002

[21] Appl. No.: 812,334

[22] Filed: Dec. 23, 1985

[51] Int. Cl.⁴ .............................................. A61N 5/00
[52] U.S. Cl. ........................................ 128/1.2; 604/63
[58] Field of Search ..................... 128/1.1–1.2, 128/653–655, 659, 7; 604/20–21, 16, 18, 60–63, 64

[56] References Cited

U.S. PATENT DOCUMENTS

| | | | |
|---|---|---|---|
| 2,621,655 | 12/1952 | Olson | 604/62 |
| 2,632,444 | 3/1953 | Kas | 604/62 |
| 2,659,369 | 11/1953 | Lipman | 604/62 |
| 3,369,542 | 2/1968 | Thaidigsman | 128/654 |
| 4,086,914 | 5/1978 | Moore | 128/1.2 |
| 4,396,021 | 8/1983 | Baumgartner | 128/7 |
| 4,402,308 | 9/1983 | Scott | 128/1.2 |
| 4,461,280 | 7/1984 | Baumgartner | 128/1.2 |
| 4,461,283 | 7/1984 | Doi | 128/7 |

Primary Examiner—Kyle L. Howell
Assistant Examiner—Angela D. Sykes

[57] ABSTRACT

A method and apparatus for implanting medication pellets, such as radioactive seeds in recessed body tissues, such as in a prostate gland. The invention utilizes structure for implanting a plurality of such pellets concurrently in accurately controlled disposition within the tissue and includes structure for effecting cauterization, or fulguration, of the tissue in the event of fluid exudation, such as bleeding.

22 Claims, 14 Drawing Figures

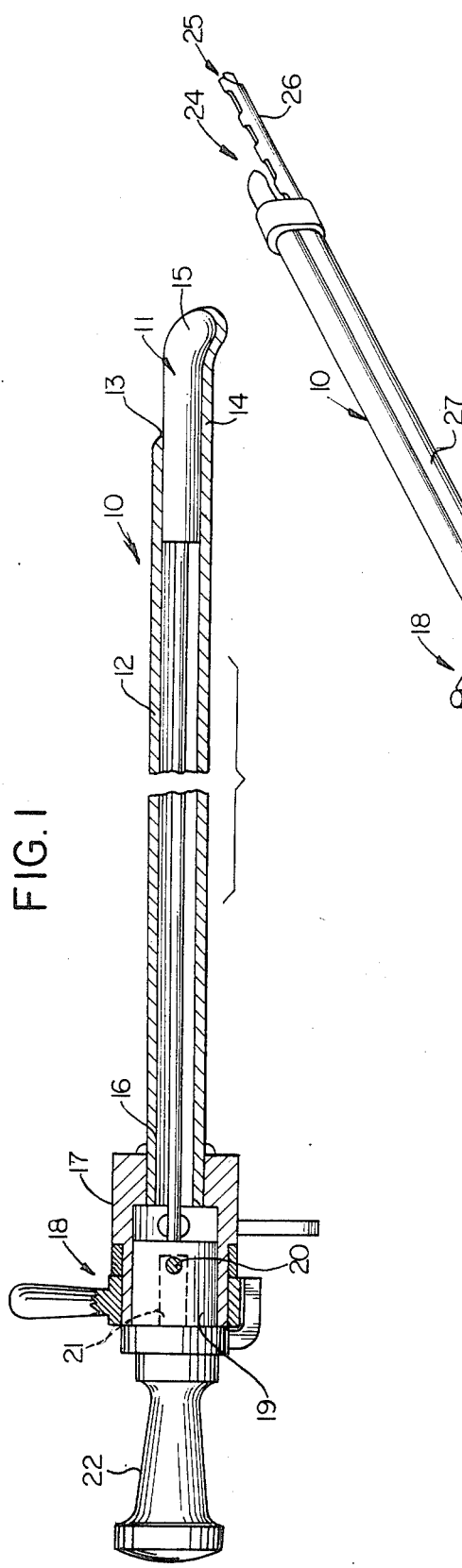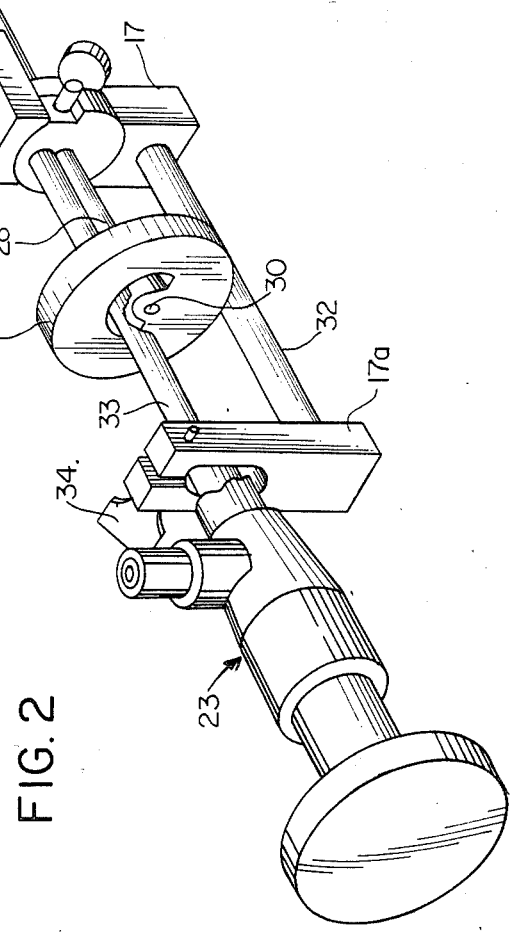

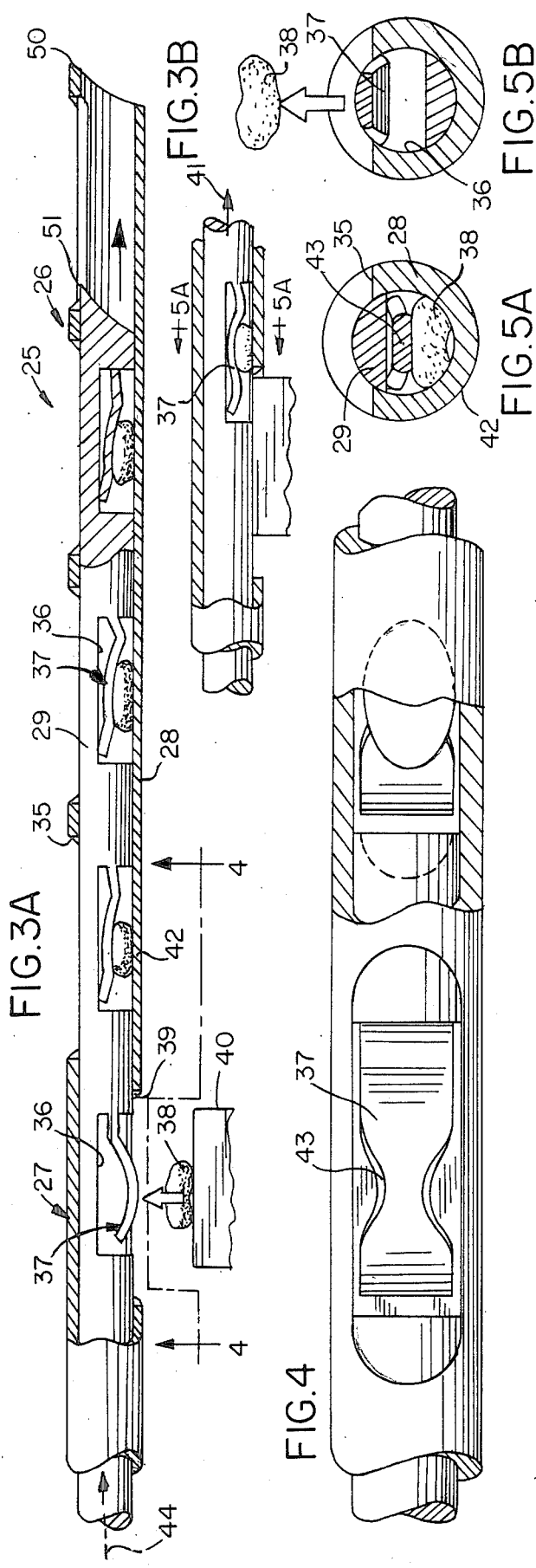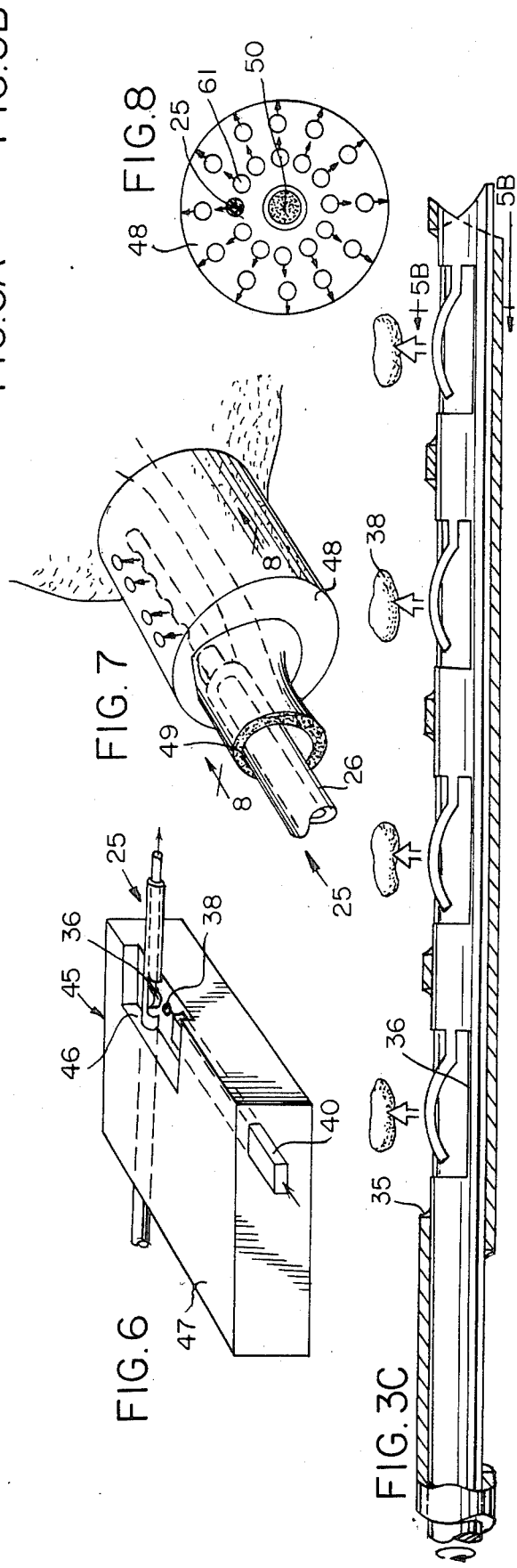

SURGICAL IMPLANTATION METHOD AND APPARATUS

BACKGROUND OF THE INVENTION

1. Field of the Invention

This invention relates to surgical methods and apparatus, and in particular to surgical methods and apparatus adapted for providing medicament pellets and the like, including radio-active seeds in recessed body tissue.

2. Description of the Background Art

The transurethral route employing a combination of endoscopy and radioactive seed implementation has been a well established treatment for prostatic carcinoma and is preferred as most prostatic carcinoma patients are in the geriatric age group.

As noted in my U.S. Pat. No. 4,461,280, a body of radioactive material, or seed, can be deposited in the prostate by the use of a biopsy needle inserted by the use of a cystoscope. This method, however, depended upon gravity and friction to rub the seed off into the tissue and, resultingly, the precise placement of the seed in the tissue could not be assured.

In that patent, the treatment method is implemented by the use of an elongated hollow sheath having an opening for retaining an obturator. The sheath and obturator are inserted into the urethra longitudinally through the penis. Once the sheath is suitably positioned, the obturator is removed and a tissue sampling device is inserted through the sheath. The physician causes the sampling device to pierce the urethra as the sampling device is guided into the prostate. The physician further inserts a digit into the rectum of the patient and uses the digit to guide the device to the appropriate location in the prostate for obtaining a biopsy.

The sampling device may also carry means for introducing medication interstitially into the prostate. This medication is usually in the form of radioactive seeds for treating prostinoma.

I have determined that the efficiency of the means for introducing medication into the prostate, as disclosed in U.S. Pat. No. 4,461,280 by rubbing seeds off into the prostate, is low and does not fully assure the deposit of all of the seeds in specific desired locations. Successive punches had to be made to deposit the seeds and their relative position with respect ot each other could not be conclusively determined, causing radioactively "hot" or "cold" spots in the gland.

Additionally, there was no assurance that the seed had released itself from the device as desired.

In addition, there is a need, at times, for cauterizing the pierced tissue to prevent bleeding and the like resulting from the piercing of the tissue.

SUMMARY OF THE INVENTION

The present invention comprehends an improved surgical technique and apparatus for loading and discharging pellets, such as medical treatment radioactive seeds, in body tissue, such as a prostate gland.

The invention comprehends a method of effecting such surgical treatment wherein the radioactive seeds are forcibly ejected into the body of tissue in accurately determinable locations.

In the illustrated embodiment, the controlled forcible ejection is effected by potentiated release means.

In the illustrated embodiment, the potentiated release means comprises spring biasing means potentiated to eject the seeds upon controlled opening of recesses in which the seeds are stored under the biasing action of the spring means.

The invention comprehends the concurrent provision of a plurality of seeds in this manner.

The invention further comprehends the provision of means for permitting selective seriatim delivery of such seeds at desired locations about a central axis of the apparatus.

The invention comprehends the provision of apparatus for effecting the controlled delivery of the pellets in the above discussed manner.

In the illustrated embodiment, means are provided for loading the seeds, or pellets, seriatim in a plurality of recesses to provide accurately controlled provision of the pellets.

The invention further comprehends the provision of such apparatus further having selectively operable means for cauterizing punctured tissue.

The means for cauterizing the tissue may be utilized in conjunction with the seed providing means, as well as independently thereof.

The improved apparatus and method of the present invention is extremely simple and economical and provides substantial improvement in the accuracy of the delivery of medicament pellets and seeds and eliminates a number of vexatious problems found in the devices of the prior art.

BRIEF DESCRIPTION OF THE DRAWING

Other features and advantages of the invention will be apparent from the following description taken in connection with the accompanying drawing wherein:

FIG. 1 is a diametric section partially in side elevation of a sheath and obturator for use in carrying out the invention;

FIG. 2 is a perspective view of an apparatus embodying the invention;

FIG. 3A is a fragmentary side elevation with portions broken away and shown in diametric section illustrating the loading of the pellets for subsequent delivery to the recessed tissue;

FIG. 3B is a fragmentary enlarged diametric section illustrating the step of retaining the loaded pellet in the recess against the biasing action of the ejection means provided therein;

FIG. 3C is a diametric section illustrating the concurrent release of the pellets from the loaded pockets by manipulation of the apparatus to permit the forcible delivery by the ejection means in the pockets;

FIG. 4 is a fragmentary side elevation illustrating an empty pocket for receiving the pellet, and including a broken-away portion illustrating in greater detail the reception of a pellet in a previously filled pocket;

FIG. 5A is an enlarged transverse section taken substantially along the line 5A—5A of FIG. 3B;

FIG. 5B is a transverse section similar to section 5A but illustrating the release of a pellet from the pocket by the ejection means provided therein;

FIG. 6 is a perspective view illustrating an apparatus for loading pellets into the pockets seriatim;

FIG. 7 is a fragmentary perspective view illustrating the ejection of the pellets from the delivery means into a body of tissue, such as a prostate gland;

FIG. 8 is a schematic end view of the prostate illustrating a distribution of a plurality of deliveries of the pellets in different portions cross-sectionally of the prostate;

BEST MODE FOR CARRYING OUT THE INVENTION

Figure 10:
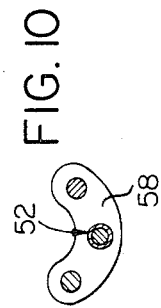
FIG. 10 is a fragmentary enlarged transverse section taken substantially along the line 10—10 of FIG. 9.
Figure 11:
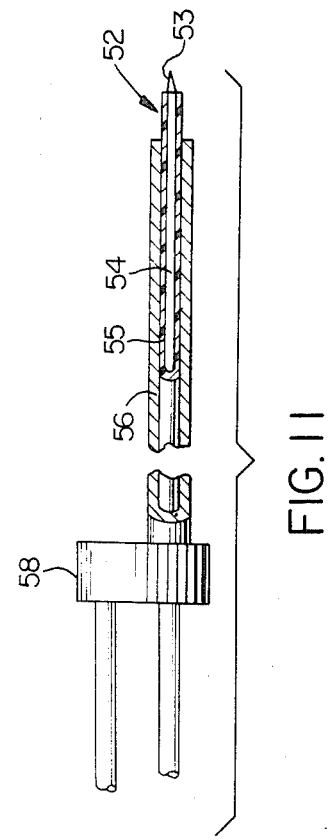
FIG. 11 is a fragmentary enlarged side elevation shown partially in longitudinal section illustrating the arrangement of the cauterizing means in the apparatus.

This invention comprises an improvement over applicant's earlier U.S. Pat. Nos. 4,396,021 and 4,461,280, which are directed to a surgical instrument and process utilizing means for extracting a biopsy sample from a prostate, or similar body tissue, and for performing medical treatment thereof. The disclosures of said Letters Patent are incorporated by reference herein.

More specifically, as shown in FIG. 1 of the drawing herein, the apparatus of the present invention includes a cystoscope generally designated 10 having an obturator portion 11 removably received within a sheath 12. In the illustrated embodiment, the apparatus is adapted for inserting solid medicament, such as radioactive seeds, into the prostate and, thus, is adapted for insertion through the urethra of the patient to adjacent the prostate.

As illustrated in FIG. 1, sheath 12 defines a distal opening 13 and the end portion 14 of the sheath is configured to retain the tip 15 removably in position as the cystoscope is inserted through the urethra.

The opposite end 16 of the sheath is mounted to a support member 17 provided with locking means generally designated 18. The locking means comprises a member 19 rotatable within the support 17. Member 19 is provided with a locking pin 20, which is selectively received in a slot 21 of the support for locking the obturator against rotation about its longitudinal axis when desired. Such rotation is effected manually by means of a gripping member 22 attached to the member 19, as shown in FIG. 1.

In use, the cystoscope 20 is firstly inserted as a unit, as shown in FIG. 1, through the urethra of the patient's penis. The end of the obturator is brought to adjacent the prostate, whereupon the obturator may be removed from the sheath and a conventional cystoscopic viewing means, generally designated 23, substituted.

The present invention is concerned with an improved method and apparatus for providing the desired deposition of medicament pellets, or radioactive seeds, as in the present case, in the tissue to be treated. As illustrated in FIG. 2, the apparatus generally designated 24 includes, in addition to the cystoscope 10, an implanter generally designated 25. The implanter comprises means for controlledly delivering the pellets, or seeds, in a novel and simple manner to the patient's tissue, such as the patient's prostate. The implanter is associated with the cystoscope in the apparatus 24 in such a manner as to permit the doctor to view the area at the end of the cystoscope adjacent a distal end portion 26 of the implanter. The implanter includes a tubular sheath 27 having an outer end 28. A cylindrical carrier 29 is movably mounted within the sheath for both axial and rotative relative movement therebetween, as shown in FIG. 3A. The distal end 30 of the carrier is connected to a knob 31 for controlled rotation and axial positioning of the carrier within the sheath while positioned externally of the patient, i.e. outwardly of the support 17.

As further illustrated in FIG. 2, the support 17 may be provided with an outboard extension 17a mounted thereto by a suitable support rod 32. The outer distal end 33 of the cystoscope may be secured against movement relative to the outboard support 17a by means of a thumbscrew 34, as shown in FIG. 2.

Thus, the apparatus 10 may be inserted through the urethra of the patient to bring the distal end 26 of the implanter to adjacent the tissue to be treated, such as the patient's prostate, and the disposition thereof may be observed by the doctor through the cystoscope means 23 for facilitated implantation of the pellets, or seeds, in the prostate.

The apparatus and method of implantation with apparatus 24 is best understood with reference to FIGS. 3A through 8. More specifically, as illustrated in FIG. 3A, end portion 28 of the sheath 27 is provided with a plurality of axially spaced, longitudinally aligned openings 35. The cylindrical carrier 29 is provided with a corresponding plurality of radially outwardly opening recesses 36. As shown in FIG. 3A, each recess is provided with an ejection means generally designated 37 for forcibly ejecting pellets, or seeds, generally designated 38, provided one each in the respective recesses 36.

As illustrated in FIG. 3A, the sheath 28 is provided with a loading aperture 39 through which the pellets are inserted one each into the recesses against the outwardly biasing force of the ejection means 37. Thus, as shown in FIG. 3A, the pellet 38 is urged into recess 36 by a suitable pressure member 40. The ejection means, as illustrated in FIG. 3, comprises, in the illustrated embodiment, a leaf spring having a convex configuration acting against the pellet to urge it outwardly from the recess under substantial force.

As illustrated in FIG. 3B, after the pellet is received in the recess 36 with the ejection spring 37 deflected radially inwardly to accommodate the pellet in the recess outwardly of the ejection spring, carrier 29 is moved axially, i.e. in the direction of arrow 41, to bring the installed pellet to longitudinally of the aperture 39, thereby capturing the pellet within the recess by the confining action of the tubular wall portion 42 of the sheath diametrically opposite the openings 35, as further illustrated in FIG. 3A.

The ejection means spring 37 extends partially outwardly through the aperture 39 when aligned therewith, as shown in FIG. 3A. The spring may have a constricted portion 43 to provide controlled ejection force, as best seen in FIG. 4.

As illustrated in FIG. 5A, the spring has a substantial ejection force and firmly retains the pellet within the recess in the loaded disposition illustrated in FIG. 5A.

As indicated above, however, carrier 29 is rotatable about the longitudinal axis 44 thereof by means of the knob 31 so as to selectively dispose the recesses 36 in the pellet-retaining disposition of FIG. 3A, or in the pellet-releasing disposition of FIG. 3C. In the pellet-releasing disposition illustrated in FIG. 3C, the alignment of the recesses 36 with the openings 35 of the implanter sheath end 26 permits the ejection means 37 to forcibly eject the pellet, or seed, 38 from the recess 36, as illustrated in each of Figures 3C and 5B. As illustrated in FIG. 3C, the ejection is effected concurrently from all of the recesses 38 so that accurate control of the spacing longitudinally of the carrier between the pellets is maintained and an accurate alignment of the implanted pellets in the body tissue is maintained.

As illustrated in FIG. 6, the loading of the carrier with the pellets may be effected by a suitable loading apparatus, such as apparatus generally designated 45. As shown in FIG. 6, the pellets 38 are loaded one each in the recesses 36 of the carrier by suitable manipulation of the pressure member 40, with the implanter 25 mounted in a suitable recess 46 of the loader body 47.

Where the apparatus is utilized in implanting radioactive seeds or the like in a prostate 48 of a patient, the end portion 26 of the implanter is brought through the patient's urethra 49 to adjacent the prostate. The distal tip 50 of the sheath 27 and the distal tip 51 of the carrier 29 are caused to be sharp so as to permit the implanter to be inserted through the wall of the urethra adjacent the prostate and to penetrate the body of the prostate longitudinally at a preselected location thereof relative to the axis of the prostate. Thus, as shown in FIG. 8, the implanter 25 may be located in a position, such as an inner 12 o'clock position relative to the center 50 of the prostate. The implanter is brought to this disposition while arranged in the pellet-retaining configuration.

The carrier is then rotated about the axis 44 so as to bring the recesses 36 to the pellet-releasing arrangement relative to the sheath openings 35 so as to concurrently implant the retained plurality of seeds 38 in the prostate, as illustrated schematically in FIG. 7.

The implanter is then removed from the prostate and a new load of pellets installed in the recesses, as discussed above, whereupon the implanter is again inserted through the urethra, with the end thereof again brought through the previous opening in the urethra to adjacent the prostate. The end of the implanter is now located in a new position relative to the axis of the prostate, such as at the 1 o'clock position 61 illustrated in FIG. 8, and a second load of pellets discharged from the recesses and implanted in the prostate in the second location. This process is repeated until the prostate receives all of the intended medication pellets such as at the different locations illustrated in FIG. 8.

At times, it is desirable to cauterize the pierced portion of the patient's tissue. Such cauterization may be effected by the process of fulguration, with the fulgurator, generally designated 52, comprising an electric heater having a tip 53 adapted to be juxtaposed to the tissue such as at the point of piercing of the prostate in the above discussed surgical operation. In the illustrated embodiment, the tip 53 is connected through a conductor 54 provided in an insulative sheath 55 in an outer metal sheath 56 of the cauterizer.

Figure 9:
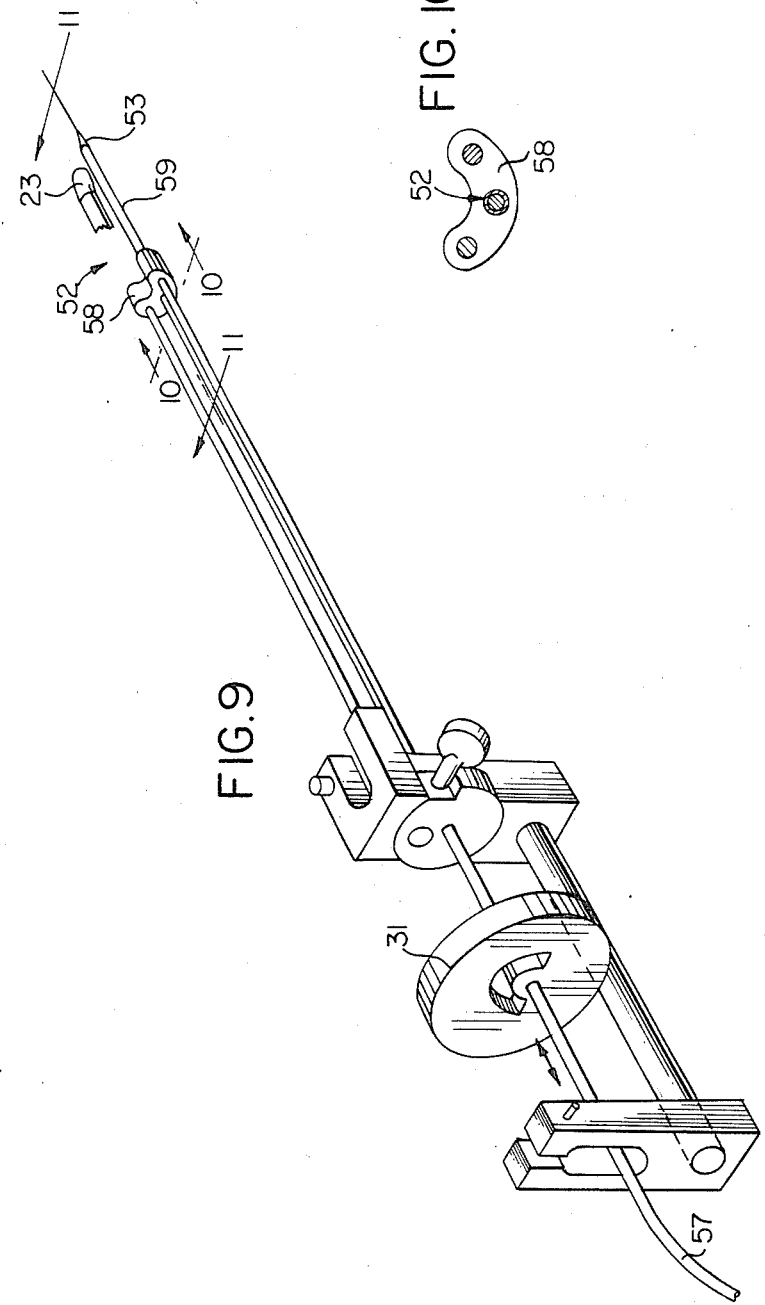
FIG. 9 is a perspective view illustrating the apparatus as arranaged for providing cauterization of the tissue.

Proper location of the fulgurator tip 53 may be effected by use of the cystoscope means 23 illustrated fragmentarily in FIG. 9. As shown in FIG. 9, the electrical connections 57 may be brought out through the center of the control knobs 31. A support 58 may be provided adjacent the distal end 59 of the cauterizer for supporting the cystoscopic means 23, as well as the cauterizing means 52.

Illustratively, the apparatus of the present invention has been utilized to implant iodine 125 seeds. The sphincter was penetrated by the implanter to permit the elasticity of the tissue to provide the above discussed parallel implantation. Different numbers of seeds were implanted at different positions about the axis of the prostate in the manner discussed above. Where bleeding was encountered, the implanter was withdrawn and replaced with the cauterizer, which functioned as a transurethral prostatic fulgurator. Approximately five seconds of coagulation was effected and good hemostasis was obtained. The implanter was reinserted at the desired site and the implantation was carried out as discussed above. Such implantation was carried out at the level of the veromontanum and slightly distal to the veromontanum through the membranous urethra down to the base of the prostate. A blood loss of less than 100 ccs. was incurred.

The method and apparatus of the present invention permits highly accurate control of the dosimetry and the uniform desired distribution of the seeds as desired commensurate with the need of medication in the prostate. Thus, the invention provides for substantially improved treatment of prostatic carcinoma and provides for improved treatment with the type of apparatus and method employed in my earlier U.S. patents as discussed above.

The foregoing disclosure of specific embodiments is illustrative of the broad inventive concepts comprehended by the invention.

I claim:

1. The method of loading and discharging pellets, such as medical treatment radioactive seeds, comprising the steps of:
   providing an elongated member with at least one transversely outwardly opening recess;
   providing forcible ejection means in each said recess;
   loading a pellet in each said recess; and
   controlledly causing said forcible ejection means to discharge said pellet transversely outwardly from each said recess.

2. The method of loading and discharging pellets of claim 1 wherein a plurality of said recesses are provided and said pellets are loaded in said member and in said recesses seriatim.

3. The method of loading and discharging pellets of claim 1 wherein a plurality of recesses are provided and said pellets are loaded in said member and in said recesses seriatim, said recesses being spaced longitudinally of the elongated member and said pellets being loaded sequentially in said recesses.

4. The method of loading and discharging pellets of claim 1 wherein said step of causing said forcible ejection means to discharge each of said pellets comprises a step of causing concurrent ejection of pellets form said recesses.

5. The method of loading and discharging pellets of claim 1 wherein said step of causing said forcible ejection means to discharge each of said pellets comprises a step of causing concurrent ejection of all of the pellets from said recesses.

6. The method of loading and discharging pellets of claim 1 wherein the placing of the pellet in the recess causes potentiation of the forcible ejection means.

7. The method of loading and discharging pellets of claim 1 wherein the placing of the pellet in the recess causes potentiation of the forcible ejection means and said step of controlledly causing discharge of the pellet includes the sub-steps of closing the recess with the pellet retained therein and the forcible ejection means potentiated to discharge the pellet upon subsequent opening of the recess to effect controlled discharge thereof.

8. The method of loading and discharging pellets of claim 1 wherein each said recess is sized to accept a preselected number of pellets.

9. The method of loading and discharging pellets of claim 1 wherein each said recess is sized to accept a single pellet.

10. The method of loading and discharging pellets of claim 1 further including the step of longitudinally inserting the elongated member into a body of tissue to dispose each said loaded pellet in said recesses within the body of tissue prior to the step of causing forcible ejection discharge thereof.

11. Apparatus for controlledly delivering pellets, such as medical treatment radioactive seeds, said apparatus comprising:
an elongated member having an end and at least one outwardly opening recess;
ejection means located in each recess for forcibly ejecting from each said recess at least one pellet adapted to be loaded thereinto;
retaining means for retaining pellets adapted to be loaded in said recess against ejection therefrom by said ejection means; and
release means for causing the retaining means selectively to release loaded pellets for ejection fully from each said recess by said ejection means.

12. The apparatus of claim 11 wherein said elongated member is provided with a plurality of longitudinally spaced such recesses each being provided with said ejection means, and said release means comprises means for causing concurrent release of pellets from said recesses.

13. The apparatus of claim 11 wherein said elongated member is provided with a plurality of longitudinally spaced such recesses each being provided with said ejection means, and said release means comprises means for causing concurrent release of all of the loaded pellets.

14. The apparatus of claim 11 wherein said end of the elongated member defines a sharp edge adapted to penetrate into a body of tissue suitably to permit subsequent longitudinal insertion of the member into the tissue to dispose each said pellet loaded recess in the body of tissue.

15. The apparatus of claim 11 wherein said ejection means comprises means for biasing the pellets outwardly from the recesses.

16. The apparatus of claim 11 wherein said ejection means comprises spring means for biasing the pellets outwardly from the recesses.

17. The apparatus of claim 11 wherein said elongated member comprises a cylindrical element and said retaining means comprises a tubular element coaxially movably receiving said elongated member and having openings for permitting said ejection means to eject the pellets outwardly therethrough as an incident of the alignment of said recesses with said openings.

18. The apparatus of claim 11 wherein said elongated member comprises a cylindrical element and said retaining means comprises a tubular element coaxially movably receiving said elongated member and having openings for permitting said ejection means to eject the pellets outwardly therethrough as an incident of the alignment of said recesses with said openings, said recesses being linearly aligned lengthwise of said elongated member.

19. The apparatus of claim 11 wherein said elongated member comprises a cylindrical element and said retaining means comprises a tubular element coaxially movably receiving said elongated member and having openings for permitting said ejection means to eject the pellets outwardly therethrough as an incident of the alignment of said recesses with said openings, said tubular element further defining a pellet-loading opening for selectively loading pellets into said recesses.

20. The apparatus of claim 11 wherein means are provided for loading pellets one each seriatim in said recesses.

21. The apparatus of claim 11 wherein said end of the elongated member defines a sharp edge adapted to penetrate into a body of tissue suitably to permit subsequent longitudinal insertion of the member into the tissue to dispose each said pellet loaded recess in the body of tissue, said apparatus further including means for selectively cauterizing the tissue at the point of penetration.

22. The method of introducing medical treatment pellets into body tissue, comprising the steps of:
providing a carrier with a plurality of recesses each having a medical treatment pellet and a pellet displacing means therein; and
concurrently causing each pellet displacing means to forcibly urge the associated pellets fully outwardly from the carrier.

* * * * *